United States Patent
Barker et al.

(10) Patent No.: US 6,945,960 B2
(45) Date of Patent: Sep. 20, 2005

(54) COMBINATION SAFETY NEEDLE ASSEMBLY AND MEDICAL APPARATUS

(75) Inventors: John Barker, Ventura, CA (US); Michael J. Botich, Oxnard, CA (US); Thor R. Halseth, Agoura, CA (US)

(73) Assignee: MDC Investment Holdings, Inc., Wilmington, DE (US)

(*) Notice: Subject to any disclaimer, the term of this patent is extended or adjusted under 35 U.S.C. 154(b) by 0 days.

(21) Appl. No.: 10/070,698

(22) PCT Filed: Nov. 29, 2000

(86) PCT No.: PCT/US00/42328

§ 371 (c)(1),
(2), (4) Date: Dec. 2, 2002

(87) PCT Pub. No.: WO01/37898

PCT Pub. Date: May 31, 2001

(65) Prior Publication Data

US 2003/0149403 A1 Aug. 7, 2003

Related U.S. Application Data

(60) Provisional application No. 60/168,146, filed on Nov. 29, 1999.

(51) Int. Cl.$^7$ .................................................. A61M 5/32
(52) U.S. Cl. ..................... 604/198; 604/110; 604/192
(58) Field of Search ........................... 604/110, 164.08, 604/192, 198, 263, 187, 197; 128/919

(56) References Cited

U.S. PATENT DOCUMENTS

| | | |
|---|---|---|
| 2,876,770 A | 3/1959 | White |
| 3,306,290 A | 2/1967 | Weltman |
| 3,463,152 A | 8/1969 | Sorenson |
| 3,890,971 A | 6/1975 | Leeson et al. |
| 4,026,287 A | 5/1977 | Haller |
| 4,333,457 A | 6/1982 | Margulies |
| 4,378,015 A | 3/1983 | Wardlaw |
| 4,392,859 A | 7/1983 | Dent |
| 4,425,120 A | 1/1984 | Sampson et al. |
| 4,507,117 A | 3/1985 | Vining et al. |
| 4,507,118 A | 3/1985 | Dent |
| 4,542,749 A | 9/1985 | Caselgrandi et al. |
| 4,573,976 A | 3/1986 | Sampson et al. |
| 4,592,744 A | 6/1986 | Jagger et al. |
| 4,631,057 A | 12/1986 | Mitchell |
| 4,664,654 A | 5/1987 | Strauss |
| 4,675,005 A | 6/1987 | DeLuccia |
| 4,692,156 A | 9/1987 | Haller |
| 4,710,170 A | 12/1987 | Haber et al. |
| 4,723,943 A | 2/1988 | Spencer |
| 4,725,267 A | 2/1988 | Vaillancourt |
| 4,737,144 A | 4/1988 | Choksi |
| 4,747,831 A | 5/1988 | Kulli |
| 4,767,413 A | 8/1988 | Haber et al. |
| 4,770,655 A | 9/1988 | Haber et al. |
| 4,804,371 A | 2/1989 | Vaillancourt |
| 4,813,426 A | 3/1989 | Haber et al. |
| 4,828,548 A | 5/1989 | Walter |
| 4,838,863 A | 6/1989 | Allard et al. |
| 4,838,869 A | 6/1989 | Allard |

(Continued)

Primary Examiner—Nicholas D. Lucchesi
Assistant Examiner—Catherine S. Williams
(74) Attorney, Agent, or Firm—Stephen H. Eland; Dann, Dorfman, Herrell and Skillman

(57) ABSTRACT

A method and apparatus are provided for using a medical device (10) comprised of a medical apparatus (20) and a needle assembly (30). The needle assembly includes a needle (70) having a sharpened tip. Preferably, the medical apparatus (20) is a standard apparatus, such as a syringe or phlebotomy device. The medical apparatus (20) includes a connector (24), such as a Luer connector. The needle assembly (30) is configured so that it can be attached to the medical apparatus (20) and the sharpened tip of the needle (70) is automatically shielded after use to prevent inadvertent contact with the contaminated needle.

19 Claims, 3 Drawing Sheets

U.S. PATENT DOCUMENTS

| | | |
|---|---|---|
| 4,850,968 A | 7/1989 | Romano |
| 4,863,435 A | 9/1989 | Sturman et al. |
| 4,874,382 A | 10/1989 | Lindemann et al. |
| 4,887,998 A | 12/1989 | Martin et al. |
| 4,894,055 A | 1/1990 | Sudnak |
| 4,898,589 A | 2/1990 | Dolgin et al. |
| 4,900,307 A | 2/1990 | Kulli |
| 4,906,236 A | 3/1990 | Alberts |
| 4,911,693 A | 3/1990 | Paris |
| 4,917,673 A | 4/1990 | Coplin |
| 4,921,486 A | 5/1990 | DeChellis et al. |
| 4,927,414 A | 5/1990 | Kulli |
| 4,927,416 A | 5/1990 | Tomkiel |
| 4,929,237 A | 5/1990 | Medway |
| 4,932,947 A | 6/1990 | Cardwell |
| 4,946,446 A | 8/1990 | Vadher |
| 4,955,868 A | 9/1990 | Klein |
| 4,955,869 A | 9/1990 | Bin |
| 4,955,870 A | 9/1990 | Ridderheim et al. |
| 4,966,592 A | 10/1990 | Burns et al. |
| 4,966,593 A | 10/1990 | Lennox |
| 4,973,316 A | 11/1990 | Dysarz |
| 4,988,339 A | 1/1991 | Vadher |
| 4,994,034 A | 2/1991 | Botich et al. |
| 5,017,187 A | 5/1991 | Sullivan |
| 5,019,044 A | 5/1991 | Tsao |
| 5,045,066 A | 9/1991 | Scheuble et al. |
| 5,046,508 A | 9/1991 | Weissler |
| 5,049,133 A | 9/1991 | Villen Pascual |
| 5,053,010 A | 10/1991 | McGary et al. |
| 5,064,419 A | 11/1991 | Gaarde |
| 5,084,018 A | 1/1992 | Tsao |
| 5,129,884 A | 7/1992 | Dysarz |
| 5,188,599 A | 2/1993 | Botich et al. |
| 5,201,720 A | 4/1993 | Borgia et al. |
| 5,346,480 A * | 9/1994 | Hess et al. .................. 604/197 |
| 5,407,431 A | 4/1995 | Botich et al. |
| 5,433,712 A * | 7/1995 | Stiles et al. .................. 604/197 |
| 5,685,863 A | 11/1997 | Botich et al. |
| 5,788,677 A | 8/1998 | Botich et al. |
| 5,800,395 A | 9/1998 | Botich et al. |
| 5,938,644 A | 8/1999 | Kirk |
| 5,980,494 A | 11/1999 | Malenchek et al. |
| 6,017,329 A | 1/2000 | Hake |
| 6,096,005 A | 8/2000 | Botich et al. |
| 6,162,197 A | 12/2000 | Mohammad |
| 6,179,812 B1 | 1/2001 | Botich et al. |
| 6,190,361 B1 | 2/2001 | Getting et al. |

* cited by examiner

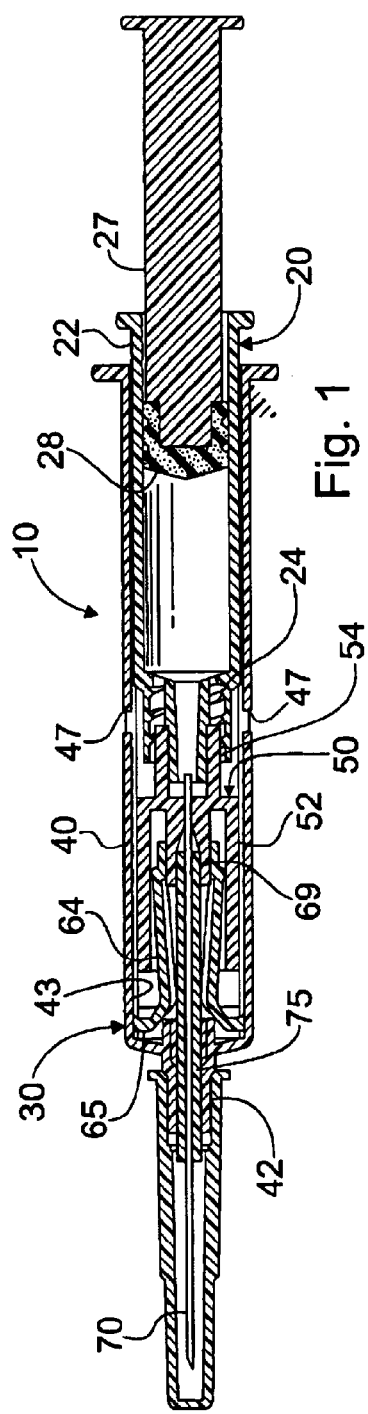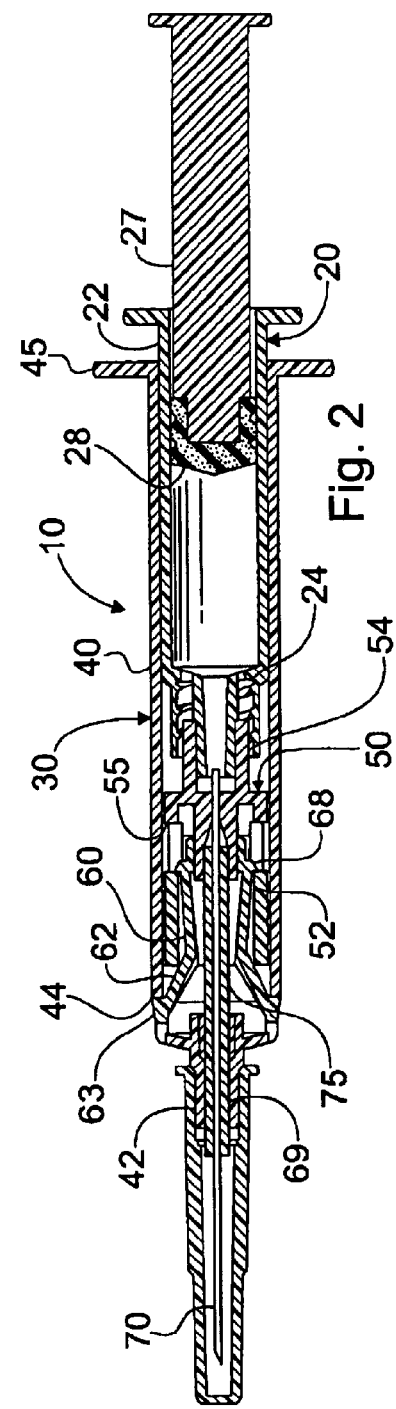

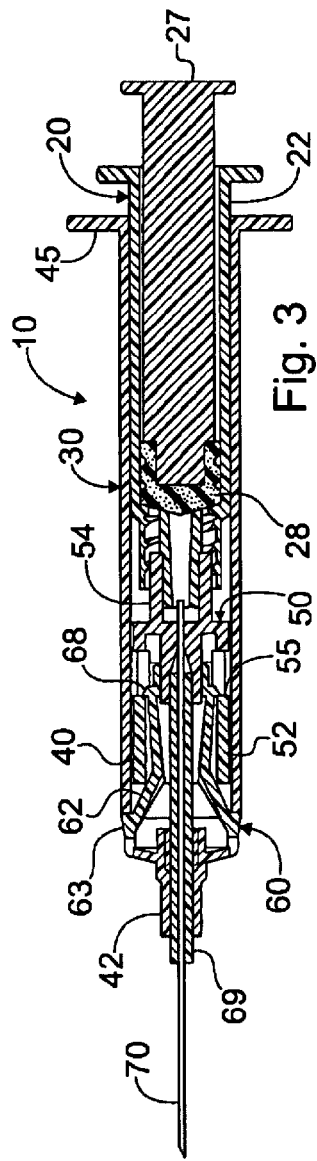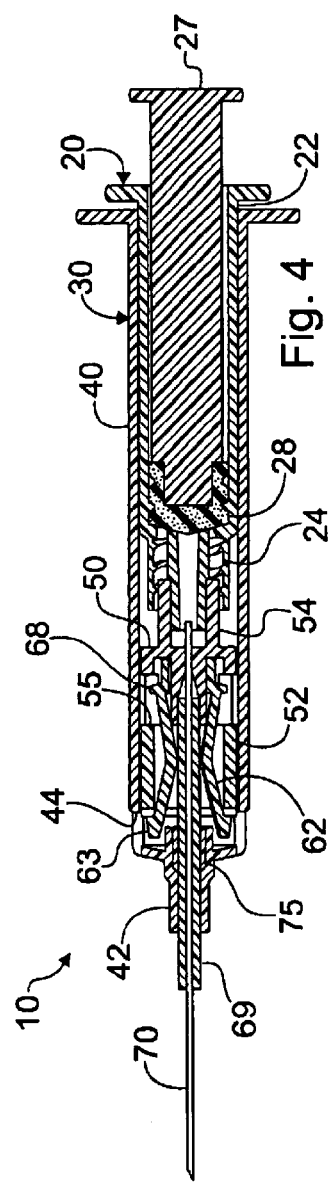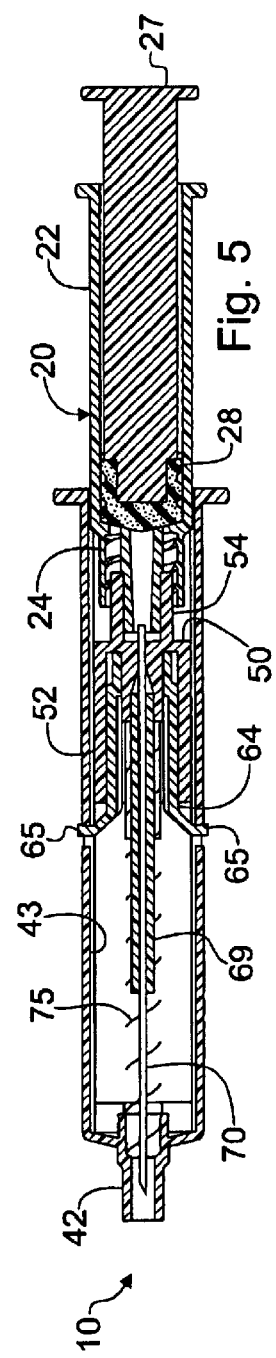

COMBINATION SAFETY NEEDLE ASSEMBLY AND MEDICAL APPARATUS

This application claims the benefit of Provisional application Ser. No. 60/168,146 filed Nov. 29, 1999.

FIELD OF THE INVENTION

The present invention relates to needle bearing medical devices. More specifically, the invention relates to such devices having a retractable needle feature for rendering the device non-reusable and safely disposable.

BACKGROUND OF THE INVENTION

Various types of medical devices employ a needle for piercing the skin of a patient for diagnostic or therapeutic purposes. One such device is a hypodermic syringe. Handling of such needle-bearing medical devices after the needle is withdrawn from the patient can result in transmission of various pathogens, most notably human immune virus (HIV), to uninfected medical personnel, due to an inadvertent needle stick. Accordingly, it is desirable to provide a device for injecting medication or withdrawing fluid, wherein the contaminated needle is enclosed after use.

DESCRIPTION OF THE DRAWINGS

All of the objects of the present invention are more fully set forth hereinafter with reference to the accompanying drawings, wherein:

FIG. 1 is a top sectional view of a combination safety needle assembly and syringe embodying aspects of the present invention;

FIG. 2 is a side sectional view of the combined safety needle assembly and syringe illustrated in FIG. 1;

FIG. 3 is a side sectional view of the combined safety needle assembly and syringe illustrated in FIG. 1, shown at the end of an injection stroke;

FIG. 4 is a side sectional view of the combined safety needle assembly and syringe illustrated in FIG. 1, shown just prior to retraction;

FIG. 5 is a top sectional view of the combined safety needle assembly and syringe illustrated in FIG. 1 shown after retraction.

DETAILED DESCRIPTION OF THE PREFERRED EMBODIMENTS

Figure 6:
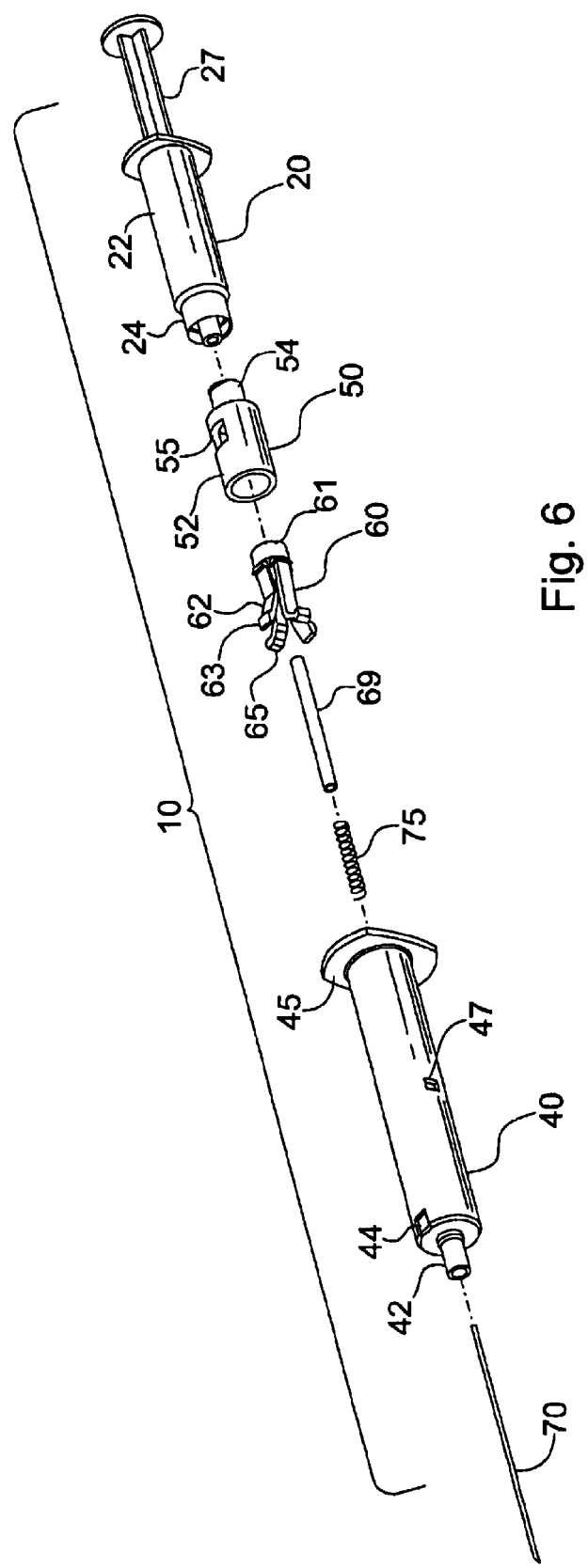
FIG. 6 is an exploded perspective view of the combination safety needle assembly and syringe illustrated in FIG. 1.

Referring now to the drawings in general and to FIG. 1 specifically, a combination medical device 20 and safety needle assembly 30 is designated generally 10. The needle assembly 30 is connectable with the medical device 20, and includes a needle 70 having a sharpened tip. After use, the needle 70 is automatically shielded to prevent inadvertent contact with the contaminated needle.

Preferably, the needle assembly 30 is configured to cooperate with a variety of standard medical devices, such as a hypodermic syringe. In this way, medical devices that are currently widely available can be used with a needle assembly that automatically shields the needle after use.

Accordingly, the needle assembly and needle assembly may be sterilized and sealed together in a single sterile package to be assembled by a medical professional prior to use. However, preferably, the needle assembly is sterilized and sealed in a sterile package separate from the needle assembly. The needle assembly can then be used with a separately packaged sterile medical device of the user's choosing.

In the drawings and the following description needle assembly 30 is illustrated and described in connection with a hypodermic syringe 20, which is the preferred combination. The syringe 20 includes a generally cylindrical housing or barrel 22 having a hollow interior forming a fluid chamber. The forward end of the barrel forms an end wall and has an opening through which medicine can flow. A connector 24, in the form of a Luer fitting, is formed on the forward end of the barrel 22. A piston 28 forms a fluid tight seal with the interior of the barrel 22. A plunger 27 connected to the piston 28 is operable to reciprocally displace the piston within the barrel 22 to draw fluid into the barrel or expel fluid from the barrel.

The needle assembly 30 includes a generally cylindrical housing 40. As discussed further below, the housing 40 operates as a shield to enclose the needle after use to prevent inadvertent contact with the contaminated needle.

The rearward end of the housing is generally open forming a socket for receiving the syringe 20. The forward end of the housing 40 forms a reduced diameter tip 42 having an opening through which the needle 70 extends. Finger tabs 45 are formed at the rearward end of the housing 40. The finger tabs provide a surface for the medical professional to engage during injection of fluid from or aspiration of fluid into the syringe 20.

The needle assembly 30 further comprises an adapter 50 for attaching the needle assembly 30 to the syringe 20. The adapter 50 comprises a generally cylindrical body 52 having a connector 54 extending from the rearward end of the body. In the present instance, the connector 54 is a threaded stem that cooperates with the Luer fitting 24 of the syringe 20. However, a variety of different connectors can be used. In addition, it may be desirable to include a lock, such as a Luer lock, for substantially permanently connecting the needle assembly 30 to the syringe 20.

The needle 70 is fixedly attached to the adapter 50, preferably by an adhesive. A spring 75 is disposed between the housing 40 and the adapter 50, biasing the adapter 50 and the attached needle 70 rearwardly. A needle retainer 60 releasably retains the needle 70 against the bias of the spring 75.

The needle retainer is disposed within the adapter 50. The needle retainer comprises a generally cylindrical hub 61 and a pair of radially deformable arms 62 extending radially outwardly from the hub. A detent 63 is formed on the end of each arm 62. The detents 63 engage sockets 44 formed in the forward end of the housing 40.

A circumferential flange 68 is formed on the exterior of the needle retainer hub 61 and engages an annular recess 55 in the adapter 50. The cooperation of the flange 68 and the recess 55 impedes rearward movement of the adapter 50 relative to the needle retainer 60. In this way, the needle retainer 60 retains the adapter 50 and the attached needle 70 against the rearward bias of the spring 75.

The adapter 50 is cooperable with the needle retainer 60 to effectuate retraction. Specifically, upon forward displacement of the adapter 50, the forward end of the adapter engages the needle retainer arms 62, thereby displacing the arms radially inwardly until the detents 63 are displaced out of registration with the sockets 44 in the housing 40. The spring 75 then propels the needle 70, needle retainer 60, adapter 50 and the syringe 20 rearwardly.

The spring 75 is a compression spring preferably made from stainless steel or other metal. The spring is sized to fit over the needle and within the arms of the needle retainer. In addition, the spring has adequate free length and spring force to ensure that the needle fully retracts into the housing 40 of the needle assembly 30.

The needle assembly 30 preferably also includes a locking mechanism for preventing continued rearward displacement of the needle 70 after retraction and for preventing re-extension of the needle after retraction. Specifically, a pair of radially deformable locking arms 64 extend from the hub 61 of the needle retainer 60. A locking tab 65 projects radially outwardly from the forward end of each locking arm 64. The locking tabs 65 engage a pair of guide slots 43 formed in the interior surface of the needle assembly housing 40. A pair of lockout sockets 47 are formed in the housing 40 adjacent the rearward end of the guide slots 43. When the needle 70 and attached components are retracted rearwardly, the locking tabs 65 engage the lockout sockets 47 to lock the needle and attached components against further axial displacement rearwardly or forwardly.

The locking arms 64 extend generally axially from the hub 61 and are disposed radially inwardly from the body 52 of the adapter 50. In this way, when the adapter body 52 is displaced forwardly into contact with the needle retainer arms 62, the adapter body 52 does not engage the locking arms 64.

In the present instance, the needle assembly 30 further comprises a rigid conduit 69 that extends between the adapter 50 and the housing 40, projecting forwardly through the tip 42 of the housing. The conduit 69 provides an alignment path for attaching the needle 70 to the adapter 50 after assembly of the remaining components of the needle assembly 30.

Configured in this way, the device 10 operates as follows. The syringe 20 is inserted into the rearward opened end of the needle assembly 30 until the Luer fitting 24 of the syringe engages the connector 54. The connector 54 is then threaded into the Luer fitting 24 to attach the needle assembly 30 to the syringe 20. The medical professional may then aspirate fluid into the syringe 20 by displacing the plunger 27 rearwardly within the barrel 22. Alternatively, the syringe 20 may be pre-filled with a measured dose of medicine. The fluid is expelled from the syringe 20 by displacing the plunger 27 forwardly.

At the end of the injection stroke, the piston 28 abuts the forward end of the interior of the barrel 22, as shown in FIG. 3. Continued forward displacement of the plunger displaces the adapter 50 forwardly, such that the adapter engages the needle retainer arms 62, displacing the arms radially inwardly until the detents 63 are displaced out of registration with the sockets 44 in the housing, as shown in FIG. 4. This releases the needle for retraction by the spring after the medical professional releases the plunger. The needle 70, adapter 50, needle retainer 60 and syringe 20 are then displaced rearwardly under the biasing force of the spring until the sharpened tip of the needle is enclosed within the housing 40, thereby shielding the contaminated needle against inadvertent contact, as shown in FIG. 5. After retraction, the lockout tabs 65 deform radially outwardly to engage the lockout sockets 47 in the housing to lock the needle against further retraction or inadvertent re-extension.

In the foregoing description, the needle 70 is described as being retracted into the housing 40. However, the motion can also be viewed as the housing 40 extending over the needle 70. Accordingly, the description uses the term retraction to describe relative motion between the needle 70 and another element, namely the housing 40, that causes the sharpened tip of the needle to be enclosed to prevent inadvertent needle sticks.

The terms and expressions which have been employed are used as terms of description and not of limitation. There is no intention in the use of such terms and expressions of excluding any equivalents of the features shown and described or portions thereof. It is recognized, however, that various modifications are possible within the scope and spirit of the invention.

For instance, the needle assembly has been described in connection with a standard hypodermic syringe that can be used to draw a dose of medicine and inject the medicine into a patient. However, the needle assembly can also be used in connection with a number of other medical devices. One such example is a phlebotomy device used for collecting blood samples. Another example is a pre-filled device, such as a syringe that is pre-filled with a measured does of medicine. Accordingly, the needle assembly can be used in connection with a variety of medical devices.

In addition, as described above in connection with the preferred embodiment, the needle and needle assembly are substantially permanently attached to the syringe. However, it may be desirable to provide a releasable connection between the medical device and the needle assembly. In this way, after use the shielded needle assembly can be safely removed and disposed of, and the medical device can be reused with a new uncontaminated needle assembly or the medical device can be used in a separate procedure. For instance, if the medical device is used to collect a fluid specimen, the needle assembly may be removed and then the medical device can be used to dispense the collected fluid into a device that analyzes the collected fluid.

What is claimed is:

1. A medical device, comprising:
   a syringe, comprising:
      a barrel;
      a plunger slidably displaceable within the barrel;
   a needle assembly, comprising:
      a housing adapted to receive the syringe;
      a needle operable between an extended position in which the needle projects forwardly from the housing and a retracted position in which the sharpened tip of the needle is enclosed within the housing;
      a biasing element biasing the needle toward the retracted position;
      a needle retainer releasably retaining the needle in the extended position against the bias of the biasing element;
      a hub that is axially displaceable relative to the needle retainer to effectuate retraction of the needle;
   wherein upon forward displacement of the syringe relative to the needle retainer, the needle is released for retraction so that the biasing element retracts the needle into the housing.

2. The medical device of claim 1 wherein the biasing element displaces the syringe rearwardly upon actuation of retraction of the needle.

3. The medical device of claim 1 comprising a connector for connecting the syringe to the needle assembly.

4. The medical device of claim 1 wherein the needle retainer comprises a radially deformable arm engaging the housing, wherein the hub displaces the arm radially inwardly to effectuate retraction of the needle.

5. A safety medical device, comprising:
- a medical apparatus comprising:
  - a housing; and
  - a first connector attached to the housing;
- a shielded needle assembly, comprising:
  - a needle having a sharpened tip;
  - a shield surrounding at least a portion of the housing, operable between a retracted position in which the sharpened tip of the needle projects forwardly from the shield and an extended position in which the sharpened tip of the needle is enclosed within the shield;
  - a second connector cooperable with the first connector to attach the needle to the housing;
  - a biasing element biasing the shield forwardly relative to the housing toward the extended position;
  - a retainer releasably retaining the shield in the retracted position against the bias of the biasing element; and
  - means for releasing the shield from the retainer in response to advancing the housing forwardly relative to the shield, wherein upon releasing the shield, the biasing element displaces the shield into the extended position.

6. The safety medical device of claim 5, wherein the needle is fixedly attached to the second connector.

7. The safety medical device of claim 5 comprising an actuator connected with the second connector, and configured to engage the needle retainer upon axial advancement of the housing relative to the shield.

8. The safety medical device of claim 5, wherein the retainer comprises a radially deformable arm.

9. The safety medical device of claim 8 comprising an actuator connected with the second connector, and configured to radially deform the retainer arm upon axial advancement of the housing relative to the shield.

10. The safety medical device of claim 5 wherein the medical apparatus comprises a plunger slidable within the housing, and the housing comprises a forward end wall such that advancing the plunger forwardly displaces the plunger into engagement with the end wall, and continued advancement of the plunger displaces the housing forwardly relative to the shield to release the shield from the retainer.

11. The safety medical device of claim 5, comprising a lock for automatically substantially permanently locking the shield after the shield is displaced into the extended position to prevent displacement of the shield relative to the needle after the shield is extended.

12. The safety medical device of claim 11 wherein the lock comprises a radially deformable locking arm and the shield comprises a recess that cooperates with the locking arm.

13. The safety medical device of claim 5 wherein the shield comprises a pair of flanges projecting radially outwardly and configured to provide a surface for a user to engage during use of the device.

14. The safety medical device of claim 5 wherein the second connector is cooperable with the first connector to substantially permanently attach the needle to the housing.

15. A method for assembling and using a safety medical device, comprising the steps of:
- providing a sterile needle assembly, comprising a needle having a sharpened tip, a shield and a hub having a first connector;
- providing a sterile medical apparatus, comprising a housing and a second connector;
- sealing the sterile needle assembly and the sterile medical apparatus within one or more containers to prevent contamination of the needle assembly and medical apparatus from becoming contaminated;
- removing the needle assembly and medical apparatus from the one or more containers;
- connecting the first connector to the second connector to attach the needle assembly to the medical apparatus;
- performing a medical procedure with the combined medical apparatus and needle assembly;
- retaining the shield against advancing over the sharpened tip of the needle during the step of performing a medical procedure;
- automatically releasing the shield and displacing the shield to enclose the sharpened tip of the needle in response to axial displacement of the hub relative to the shield.

16. A method for assembling and using a safety medical device, comprising the steps of:
- providing a sterile needle assembly, comprising a needle having a sharpened tip, a shield and a hub having a first connector;
- providing a sterile medical apparatus, comprising a barrel for receiving medicine, a plunger slidable within the barrel, and a second connector;
- sealing the sterile needle assembly and the sterile medical apparatus within one or more containers to prevent the needle assembly and medical apparatus from becoming contaminated;
- removing the needle assembly and medical apparatus from the one or more containers;
- connecting the first connector to the second connector to attach the needle assembly to the medical apparatus;
- injecting medicine from the barrel and through the attached needle assembly by displacing the plunger forwardly within the barrel;
- retaining the shield against advancing over the sharpened tip of the needle during the step of injecting medicine;
- axially displacing the hub relative to the shield to automatically releasing the shield and displacing the shield to enclose the sharpened tip of the needle in response to axial displacement of the plunger.

17. The method of claim 16, wherein the first connector and second connector are cooperating Luer connectors.

18. The method of claim 16 wherein the needle assembly comprises a biasing element, and the step of automatically releasing the shield and displacing the shield comprises automatically advancing the shield with the spring after the shield is released.

19. The method of claim 16 comprising the step of automatically locking the shield to prevent axial displacement of the shield relative to the needle after the shield encloses the sharpened tip of the needle.

* * * * *